United States Patent [19]

Shu

[11] Patent Number: 5,780,852

[45] Date of Patent: Jul. 14, 1998

[54] DIMENSION MEASUREMENT OF A SEMICONDUCTOR DEVICE

[75] Inventor: Jing-Shing Shu, Dallas, Tex.

[73] Assignee: Texas Instruments Incorporated, Dallas, Tex.

[21] Appl. No.: 824,856

[22] Filed: Mar. 26, 1997

Related U.S. Application Data

[60] Provisional application No. 60/014,123 May 25, 1996.
[51] Int. Cl.[6] .......................... G01N 1/32; G01N 23/225
[52] U.S. Cl. ............................................ 250/304; 250/304
[58] Field of Search ...................................... 250/307, 304

[56] References Cited

U.S. PATENT DOCUMENTS

| | | | |
|---|---|---|---|
| 4,670,650 | 6/1987 | Matsuzawa et al. | 250/307 |
| 4,733,074 | 3/1988 | Kato | 250/307 |

*Primary Examiner*—Jack I. Berman
*Attorney, Agent, or Firm*—Mark A. Valetti; W. James Brady; Richard L. Donaldson

[57] ABSTRACT

A feature (24) of a semiconductor device (10) is formed in a photoresist (14). To accurately measure a dimension (26) of the feature (24), portions of the photoresist (14) are removed to provide a reduced thickness (34) of the photoresist (14). The ratio between the reduced thickness (34) and the dimension (26) allows for more accurate dimension measurement of the feature (24) of the semiconductor device (10).

20 Claims, 3 Drawing Sheets

DIMENSION MEASUREMENT OF A SEMICONDUCTOR DEVICE

This application claims priority under 35 USC § 119(e)(1) of provisional application Ser. No. 60/014,123, filed Mar. 25, 1996.

TECHNICAL FIELD OF THE INVENTION

This invention relates in general to the field of semiconductor fabrication and more specifically to dimension measurement of a semiconductor device.

BACKGROUND OF THE INVENTION

Semiconductor devices include a multitude of features formed using a variety of fabrication techniques. One technique for forming features on a semiconductor device is called photolithography. This technique imparts energy on portions of a photoresist to selectively remove the photoresist. The resulting patterned photoresist allows further fabrication of the layer underlying the photoresist.

Patterning accuracy using photolithography techniques has improved with the demand for higher feature densities on semiconductor devices. For example, features formed in a photoresist may have dimensions that measure less than 0.3 microns. To ensure accurate and consistent patterning, a scanning electron microscope (SEM) may measure the dimensions of features formed in a photoresist. However, electron charging of a non-conductive photoresist may interfere with the collection of secondary electrons at the SEM and distort dimension measurement. Furthermore, the increasing ratio of the photoresist thickness to the dimension of the feature makes the retrieval of secondary electrons at the SEM more difficult. This problem may be exacerbated when measuring dimensions of features with limited spacing, such as contact holes.

SUMMARY OF THE INVENTION

In accordance with the present invention, the disadvantages and problems associated with dimension measurement of a semiconductor device have been substantially reduced or eliminated.

In accordance with one embodiment of the present invention, a method for measuring a dimension of a feature formed in a photoresist is disclosed. The method includes: forming a filler in the feature; removing portions of the filler and the photoresist to reduce the photoresist thickness; removing the filler in the feature; and measuring the dimension of the feature.

In accordance with another embodiment of the present invention, a semiconductor device includes a layer of material to be patterned. A photoresist overlies the layer and defines a feature with a dimension of less than 0.3 microns. Portions of the photoresist have been removed to produce a photoresist thickness no greater than 1.0 microns.

In accordance with another embodiment of the present invention, a method for selecting a patterning condition is disclosed. The method includes: providing a test piece having a layer of material and an overlying photoresist with a number of regions and a photoresist thickness; patterning each region of the photoresist with a feature using a corresponding patterning condition; removing portions of the photoresist to reduce the photoresist thickness; measuring, in each region, a dimension of the feature; and selecting a patterning condition in response to the step of measuring.

Important technical advantages of the present invention include accurate dimension measurement of a feature formed in a photoresist of a semiconductor device. This is accomplished by reducing the photoresist thickness before measuring the dimensions of the feature. In one embodiment, a ratio of approximately three or less between the reduced photoresist thickness and the dimension of the feature promotes more accurate dimension measurement. For example, a scanning electron microscope (SEM) may measure features with dimensions of 0.3 microns or less when the photoresist thickness has been reduced to 1.0 microns or less.

Another important technical advantage of the present invention includes accurate dimension measurement without sacrificing photoresist thickness in later fabrication. First, the features are formed on a sacrificial test piece and measured by reducing the photoresist thickness. After confirming the geometry of the featured formed using the test piece, the full photoresist thickness may be used to fabricate the semiconductor device.

Another important technical advantage of the present invention includes a technique for selecting a patterning condition for semiconductor device fabrication. This is accomplished by patterning designated regions on a test piece using a different patterning condition by varying, for example, the exposure energy and focus of a stepper. After patterning, the photoresist thickness is reduced for dimension measurement. The dimensions of the feature in each region may then be measured, and the region with the most desirable feature geometry selected. The fabrication of the semiconductor device uses the patterning condition corresponding to the selected region. Other important technical advantages are readily apparent to one skilled in the art from the following figures, descriptions, and claims.

BRIEF DESCRIPTION OF THE DRAWINGS

For a more complete understanding of the present invention, and for further features and advantages, reference is now made to the following description taken in conjunction with the accompanying drawings, in which.

DETAILED DESCRIPTION OF THE INVENTION

FIGS. 1A–1E illustrate a method for forming a feature in a photoresist for measurement. The feature may be a hole, channel, via, line, or other structure that allows further fabrication of the underlying material. After performing the method illustrated in FIGS. 1A–1E, the measurement of the dimensions of the feature may be performed by a scanning electron microscope (SEM), an electron backscattering detection device, an optical device, or any other device that can measure a dimension of the feature formed in the photoresist. This method may be used during research and development, prototyping, or production of memory, such as dynamic random access memories (DRAMs), static random access memories (SRAMs), logical elements, microprocessors, controllers, or any other semiconductor device.

Figure 1A:
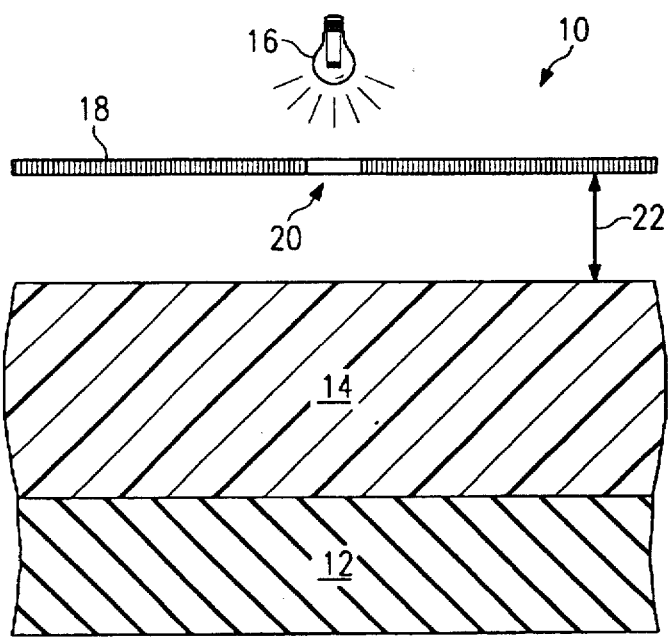
FIGS. 1A–1E illustrate a method for forming a feature in a photoresist for measurement.

FIG. 1A illustrates a cross section of a portion of a semiconductor device 10 during fabrication that includes a layer 12 underlying a photoresist 14. Layer 12 may be a substrate comprising silicon, silicon on insulator, or other appropriate material. Furthermore, layer 12 may be a non-conducting layer, a conducting layer, or any other suitable layer of material used in the fabrication of semiconductor device 10. Generally, layer 12 may be any material to be patterned using photoresist 14.

An energy source 16 emits visible light, electrons, X-rays, or any other suitable energy to be imparted on photoresist 14. A patterning film 18 disposed between photoresist 14 and energy source 16 selectively passes energy from energy source 16 to photoresist 14. In the particular embodiment illustrated in FIG. 1A, energy from energy source 16 passes through patterning film 18 at region 20 and impinges on a selected portion of photoresist 14. Energy source 16 may be adjusted to vary the intensity, quality, or duration of energy imparted on photoresist 14. Moreover, a separation 22 between photoresist 14 and patterning film 18 may be varied to change the quality or form of energy imparted on photoresist 14.

In one embodiment, semiconductor device 10 is housed in a stepper which includes energy source 16 and appropriate mounting for patterning film 18. The stepper may include a variety of settings relating to energy source 16, separation 22, the focus or depth of field of energy imparted on photoresist 14, or any other suitable setting that adjusts the nature, quality, character, precision, or accuracy of energy imparted on selected portions of photoresist 14.

The energy generated by energy source 16 that passes through patterning film 18 and imparts on photoresist 14 causes selected portions of photoresist 14 to be removed. Photoresist 14 may be a positive or negative photoresist that is sensitive to visible light, electrons, X-rays, or any other suitable energy. For example, portions of a positive photoresist material may be removed after exposure, whereas portions of a negative photoresist may remain after exposure. The removal of selected portions of photoresist 14 may be performed by using an appropriate developing solution, by an etch process selective to those portions of photoresist 14 that are not to be removed, or by any other suitable removal process.

Figure 1B:
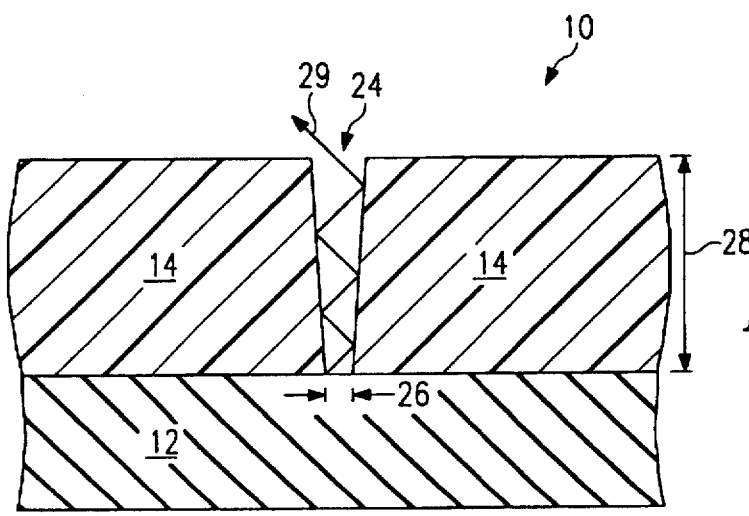

FIG. 1B illustrates semiconductor device 10 after developing and drying photoresist 14. In this embodiment using a positive photoresist material, a feature 24 is formed in photoresist 14 having a location and geometry that corresponds to region 20 in patterning film 18 that passed energy from energy source 16. Feature 24 may be a hole, channel, via, line, or any other feature appropriate for fabrication of semiconductor device 10. A dimension 26 defines, at least in part, the portion of layer 12 exposed after forming feature 24. The monitoring and control of dimension 26 may be important for later patterning of layer 12 using photoresist 14. For example, if later patterning of layer 12 includes an etch process, then dimension 26 defines that portion of layer 12 exposed to the etch. Dimension 26 may be referred to as a critical dimension of feature 24 since it defines the geometry of exposed portions of layer 12.

The structure of photoresist 14 as shown in FIG. 1B may be hardened by a variety of techniques. In one embodiment, semiconductor device 10 may be subjected to heat to remove some or all of the residual water or developing solution within photoresist 14. Another technique, exposes the surfaces of photoresist 14 to energy that decomposes and recombines these surfaces to improve the durability of photoresist 14 and to maintain the geometry of feature 24. This hardening process by exposing photoresist 14 to visible light, ultraviolet light, or other energy may be performed in the ambient air, a vacuum, or a nitrogen environment. The present invention contemplates hardening of photoresist 14 using one or more of the techniques described above.

At this stage of the process, the ratio between thickness 28 of photoresist 14 and dimension 26 is large, which presents difficulties in accurately measuring dimension 26. For example, a scanning electron microscope (SEM) may measure dimension 26 of feature 24. An SEM normally uses electron beams with potentials in the range of 0.5 Kev to 2.0 Kev under a vacuum of $1 \times 10^6$ torr. The SEM emits primary electrons onto semiconductor device 10 and collects secondary electrons reflecting off the surfaces of semiconductor device 10. By scanning the primary electrons over feature 24, the collected secondary electrons correspond to the geometric features of feature 24, including dimension 26. The information generated by the SEM may then be processed to determine the exact dimensions of feature 24.

The quality of signals received by the SEM, and therefore the quality of the dimension measurement, depends on the material, shape, size and aspect ratio of feature 24 under study. In addition, the operation parameters of the SEM itself, such as operational voltage, probe current, magnification, and other suitable settings may impact the quality and accuracy of the measurement. For line features, the secondary electrons may be collected more readily as the SEM scans due to the wider spaces. However, a contact hole with a limited spacing presents a more difficult measurement problem for the SEM. As shown in FIG. 1B, the aspect ratio of feature 24 (photoresist thickness 28 divided by dimension 26) is relatively large, which may interfere with the retrieval of secondary electrons. An exemplary secondary electron path 29 illustrates the effect of a large aspect ratio of feature 24. Furthermore, electron charging of photoresist 14 along the height of feature 24 may interfere with the collection of secondary electrons at the SEM and further distort dimension measurement.

Figure 1C:
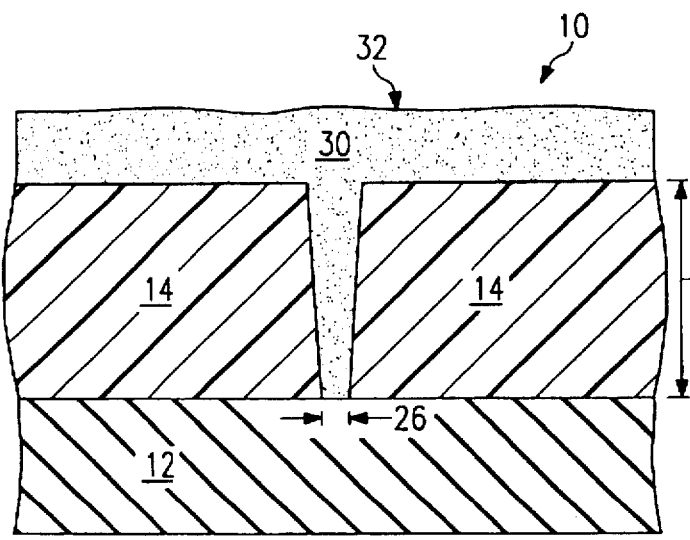

FIG. 1C illustrates a filler 30 formed in feature 24 and overlying photoresist 14. Filler 30 may be a polymer solution, such as an organic polyvinyl alcohol, that is water soluble. Furthermore filler 30 may be an inorganic silicate, such as a suitable pre-cursor to spin-coated glass. In another embodiment, filler 30 may be formed by vapor deposition using a chemical vapor deposition (CVD) technique or a physical vapor deposition technique.

Generally, filler 30 may be any material that is substantially inert to photoresist 14 and that may be deposited or formed so that its surface 32 is relatively planar. Additionally, the material for filler 30 may be chosen so that its solvent is substantially inert to photoresist 14. Filler 30 may be planarized using a reflow process, spin coating, mechanical or chemical polishing, a planarization etch, or other appropriate planarization techniques. However, filler 30 may be formed with or without concern for a planarized surface 32, if later planarization techniques are performed as described below with reference to FIG. 1D.

Figure 1D:
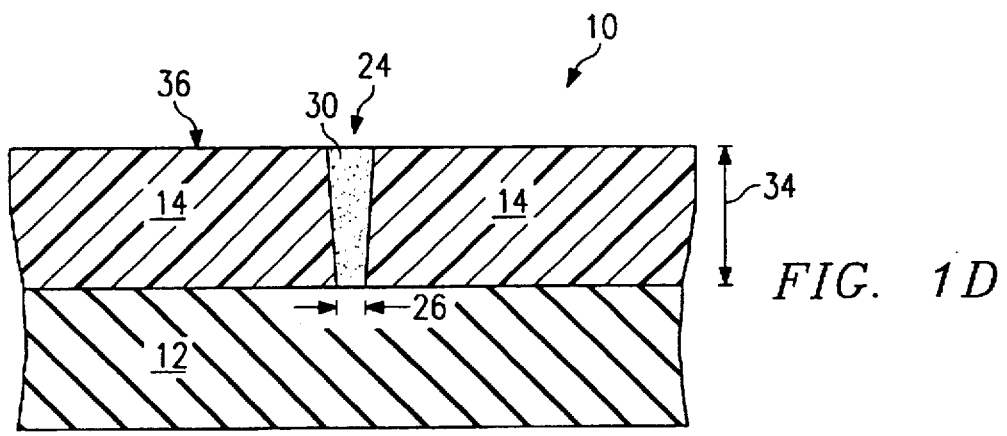

FIG. 1D illustrates semiconductor device 10 after removing portions of filler 30 overlying photoresist 14 and portions of photoresist 14. This may be performed using a plasma or dry etch, a chemical mechanical planarization (CMP) technique, a polishing technique, or any other suitable process to remove portions of filler 30 and photoresist 14. If surface 32 of filler 30 is substantially planar, a consistent timed etch process produces a surface 36 of photoresist 14 that is also substantially planar. It is desirable to remove as much of photoresist 14 while still maintaining the geometry geometries at the sidewalls and at the bottom of feature 24 for dimension measurement.

In addition to removing portions of filler 30 and photoresist 14, a planarization technique may be included to planarize the surface 36 of photoresist 14. This planarization may be accomplished using any of the techniques described above with respect to FIG. 1C. Alternatively, planarization of filler 30 as described above with reference to FIG. 1C may obviate the need for additional planarization with respect to FIG. 1D. The present invention contemplates one or more planarization steps before or after removing portions of filler 30 overlying photoresist 14 to establish a substantially uniform and reduced thickness 34 of photoresist 14.

Figure 1E:
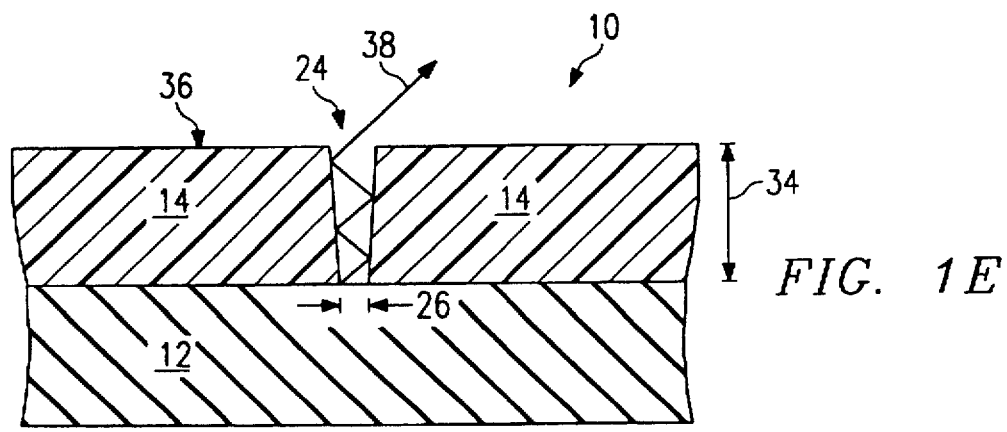

FIG. 1E illustrates semiconductor device 10 after removing filler 30 from feature 24. The removal of filler 30 may be performed using an appropriate solvent, a dry plasma etch selective to photoresist 14, or any other appropriate technique. A measurement device such as a scanning electron microscope (SEM) can more accurately determine dimension 26 due to the reduced aspect ratio of feature 24 (reduced thickness 34 divided by dimension 26). This provides a shorter and more direct secondary electron path 38 from the bottom of feature 24 to the measurement device than the secondary electron path 29 of FIG. 1B.

To improve dimension measurement, the present invention reduces the aspect ratio of feature 24 under measurement by reducing the thickness 34 of photoresist 14. It should be understood that reduced thickness 34 of photoresist 14 is for measurement purposes, but later fabrication of semiconductor device 10 may be performed using the original thickness 28 of photoresist 14. The original thickness 28 of photoresist 14 may be desirable for the next processing step to pattern layer 12. For example, an etch process to pattern layer 12 may benefit from a thicker photoresist 14.

Figure 2:
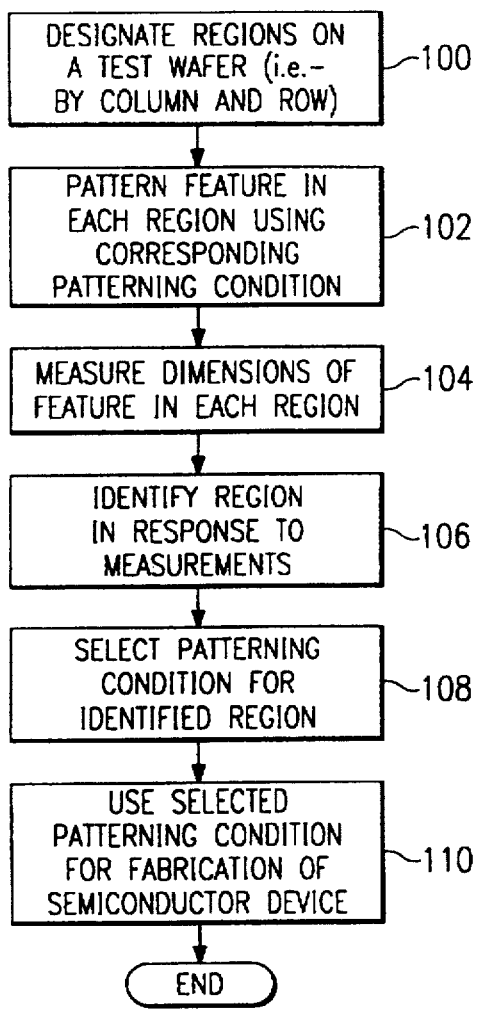
FIG. 2 illustrates a flow chart of a method for selecting a patterning condition.

FIG. 2 illustrates a flow chart of a method for selecting a patterning condition for semiconductor device 10. The method begins at step 100 with a designation of regions on a test piece, such as a test wafer. This may be performed by defining a two-dimensional grid with a first axis of the grid corresponding to a first patterning parameter and a second axis of the grid corresponding to a second patterning parameter. Patterning parameters may include exposure energy, focus, depth of field, other stepper settings, or any other suitable patterning parameter that can be varied during patterning of photoresist 14. The collective patterning parameters for a given region on the test piece define a patterning condition.

In one embodiment, a nine by nine grid defines eighty-one different regions, each region corresponding to a specific patterning condition of exposure energy and focus. Each row of the grid may correspond to a focus setting of a stepper used for patterning photoresist. For example, the first row may correspond to a −2.0 micron focus setting with each subsequent row incremented by +0.3 microns. Each column may correspond to an exposure energy setting of the stepper. For example, the first column may correspond to ten mj/cm$^2$ with each subsequent column incremented by five mj/cm$^2$. The regions arranged in such a grid represent a variety of patterning conditions with different exposure energies and different focuses.

At least one feature is patterned in each region using the corresponding patterning condition at step 102. Each region should be patterned with at least one common feature for comparison to other regions. Dimensions of features in each region are measured at step 104. For example, for each region with a different patterning condition, dimension 26 of feature 24 is measured by a scanning electron microscope (SEM). Many of the details embodied in step 104 are described below with reference to FIG. 3.

Based on the measurements performed in step 104, a region that yielded the most desirable dimension 26 of feature 24 is identified at step 106. For example, the design of feature 24 may have called for dimension 26 to be 0.2 microns. In this one-dimensional example, step 106 may identify the region that produced feature 24 with dimension 26 that most closely met the targeted dimension of 0.2 microns. The identification of a region in step 106 may be based on a comparison between the measured values of one or more dimensions of one or more features and their associated target values. Furthermore, step 106 may depend on other considerations, such as the time, expense, or repeatability of a patterning condition, as well as the resulting profile, sharpness, durability, or other suitable measure of photoresist 14 or feature 24.

Once the region that yields the best patterning results is identified, the patterning condition for the identified region is selected at step 108. The fabrication of semiconductor device 10 at step 110 proceeds with the selected patterning condition. In one embodiment, a sacrificial test wafer allows selection of a patterning condition that may be used to fabricate semiconductor device 10 on many additional wafers.

Figure 3:
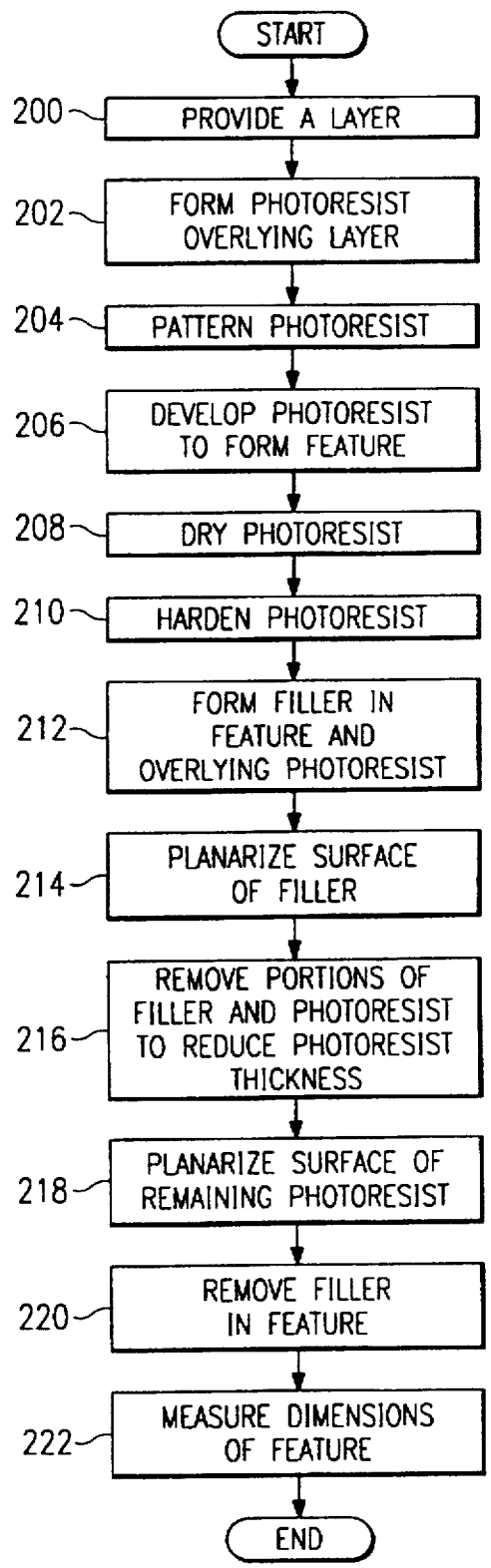
FIG. 3 illustrates a flow chart of a method for measuring a dimension of a feature formed in a photoresist.

FIG. 3 illustrates a flow chart of a method for measuring dimension 26 of feature 24 formed in photoresist 14. The method begins at step 200 by providing layer 12 that is eventually to be patterned. A photoresist 14 is formed overlying layer 12 at step 202. Photoresist 14 is then patterned by passing energy generated by energy source 16 through patterning film 18 to selected portions of photoresist 14 at step 204. As described above with reference to FIG. 2, different regions on a test wafer may be patterned using different patterning conditions.

After exposing selected portions of photoresist 14 to energy from energy source 16, photoresist 14 is developed to form feature 24 at step 206. This may be performed by a liquid developer at, for example, a constant time and temperature, or by using an appropriate dry etch that is selective to those portions of photoresist 14 that are not to be removed. Photoresist 14 is then dried using a spin process or other suitable technique at step 208. Photoresist 14 is hardened at step 210. The resulting patterned photoresist 14 has thickness 28 and defines feature 24 with dimension 26.

Filler 30 is formed in feature 24 and overlying photoresist 14 at step 212. During the process of forming filler or in a separate process, surface 32 of filler 30 is planarized using any appropriate technique described above at step 214. Portions of filler 30 and photoresist 14 are removed at step 216 to produce semiconductor device 10 with a reduced thickness 34 of photoresist 14 at step 216. In addition to or as an alternative to step 214, surface 36 of the remaining photoresist 14 may be planarized at step 218.

Filler 30 in feature 24 is removed at step 220. This may be performed using an appropriate solvent or a dry plasma etch selective to photoresist 14. Upon removing filler 30 from feature 24, dimension 26 of feature 24 may be measured using an SEM or other appropriate device at step 222. A reduced thickness 34 of photoresist 14 decreases the aspect ratio of feature 24, which allows a more accurate measurement of dimension 26.

Although the present invention has been described with several embodiments, a myriad of changes, variations, alterations, transformations, and modifications may be suggested to one skilled in the art, and it is intended that the present invention encompass such changes, variations, alterations, transformations, and modifications as fall within the spirit and scope of the appended claims.

What is claimed is:

1. A method for measuring a dimension of a feature formed in a photoresist having a photoresist thickness, comprising:
   forming a filler in the feature;
   removing portions of the filler and the photoresist to reduce the photoresist thickness;
   removing the filler in the feature; and
   measuring the dimension of the feature.

2. The method of claim 1, further comprising the step of hardening the photoresist before the step of forming a filler in the feature.

3. The method of claim 1, further comprising the step of planarizing the surface of the filler before removing portions of the filler and the photoresist.

4. The method of claim 1, wherein:
   the dimension of the feature is less than 0.3 microns; and
   the photoresist thickness, after removing portions of the filler and the photoresist, is less than 1.0 microns.

5. The method of claim 1, wherein the ratio of the photoresist thickness, after removing portions of the filler and the photoresist, to the dimension of the feature is less than or equal to three.

6. The method of claim 1, wherein the step of measuring is performed by a scanning electron microscope.

7. The method of claim 1, wherein the filler comprises an organic polymer solution.

8. The method of claim 1, wherein the dimension comprises the diameter of a contact hole.

9. A semiconductor device, comprising:
   a layer of material to be patterned; and
   a photoresist overlying the layer and defining a feature with a dimension of less than 0.3 microns, wherein portions of the photoresist have been removed to produce a photoresist thickness of less than 1.0 microns for measuring the dimension of the feature.

10. The semiconductor device of claim 9, wherein the ratio of the photoresist thickness to the dimension of the feature is less than or equal to three.

11. The semiconductor device of claim 9, wherein the photoresist comprises an organic material.

12. The semiconductor device of claim 9, wherein the dimension comprises the diameter of a contact hole.

13. The semiconductor device of claim 9, further comprising a filler formed in the feature.

14. The semiconductor device of claim 9, further comprising a filler formed in the feature, wherein the filler comprises an organic polymer solution.

15. A method for selecting a patterning condition, comprising:
   providing a test piece having a layer of material and an overlying photoresist with a plurality of regions and a photoresist thickness;
   patterning each region of the photoresist with a feature using a corresponding patterning condition;
   removing portions of the photoresist to reduce the photoresist thickness;
   measuring, in each region, a dimension of the feature; and
   selecting a patterning condition in response to the step of measuring.

16. The method of claim 15, wherein:
   the dimension of the feature is less than 0.3 microns; and
   the photoresist thickness, after removing portions of the photoresist, is less than 1.0 microns.

17. The method of claim 15, wherein the ratio of the photoresist thickness, after removing portions of the photoresist, to the dimension of the feature is less than or equal to three.

18. The method of claim 15, wherein the step of measuring is performed by a scanning electron microscope.

19. The method of claim 15, wherein the patterning condition comprises:
   a selected exposure energy of a stepper; and
   a selected focus setting of the stepper.

20. The method of claim 15, wherein each region of the photoresist corresponds to a grid location defined by a first value and a second value, the first value corresponding to a selected exposure energy of a stepper and the second value corresponding to a selected focus setting of the stepper.

* * * * *